(12) United States Patent
Holt et al.

(10) Patent No.: US 8,119,409 B2
(45) Date of Patent: Feb. 21, 2012

(54) MERCURY IONIC GAS STANDARD GENERATOR FOR A CONTINUOUS EMISSIONS MONITORING SYSTEM

(75) Inventors: Mark Wayne Holt, Emmaus, PA (US); William Howard Eberhardt, Cherry Hill, NJ (US)

(73) Assignee: General Electric Company, Schenectady, NY (US)

( * ) Notice: Subject to any disclaimer, the term of this patent is extended or adjusted under 35 U.S.C. 154(b) by 653 days.

(21) Appl. No.: 11/872,542

(22) Filed: Oct. 15, 2007

(65) Prior Publication Data

US 2009/0098656 A1   Apr. 16, 2009

(51) Int. Cl.
*G01N 33/20* (2006.01)
*B05B 17/04* (2006.01)
(52) U.S. Cl. .......... 436/81; 239/136; 239/303; 239/337; 239/8
(58) Field of Classification Search ............. 239/136, 239/303, 337, 8; 436/81, 53; 422/81
See application file for complete search history.

(56) References Cited

U.S. PATENT DOCUMENTS

| | | | |
|---|---|---|---|
| 5,337,962 A | | 8/1994 | Erb et al. |
| 5,372,754 A | * | 12/1994 | Ono .............................. 261/142 |
| 5,630,878 A | * | 5/1997 | Miyamoto et al. ............ 118/715 |
| 5,690,743 A | * | 11/1997 | Murakami et al. ............ 118/715 |
| 5,981,295 A | * | 11/1999 | Schmitt .......................... 436/180 |
| 6,761,109 B2 | | 7/2004 | Newman et al. |
| 6,974,126 B2 | | 12/2005 | Newman et al. |
| 2004/0175579 A1 | * | 9/2004 | Smith et al. .................... 428/446 |
| 2005/0061110 A1 | * | 3/2005 | Schaedlich et al. ............. 75/670 |
| 2005/0084976 A1 | * | 4/2005 | Baldwin et al. .................. 436/81 |
| 2007/0178015 A1 | * | 8/2007 | Schaedlich et al. ........... 422/100 |

FOREIGN PATENT DOCUMENTS

EP   0923985 A1   6/1999

* cited by examiner

*Primary Examiner* — Robert J Hill, Jr.
*Assistant Examiner* — Dwan A Gerido
(74) *Attorney, Agent, or Firm* — Armstrong Teasdale LLP

(57) ABSTRACT

A mercury ionic gas standard generator for use in the continuous emissions monitoring of exhaust flue gas streams is disclosed. More specifically, the mercury ionic gas standard generator uses a reservoir being coated with an inert silicon-based coating for transporting a volume of an aqueous ionic mercury solution to a liquid mass flow controller and vaporizer.

11 Claims, 1 Drawing Sheet

MERCURY IONIC GAS STANDARD GENERATOR FOR A CONTINUOUS EMISSIONS MONITORING SYSTEM

BACKGROUND OF THE INVENTION

This invention relates generally to a mercury ionic gas standard generator for use in the continuous emissions monitoring of exhaust flue gas streams. More specifically, the present disclosure relates to the use of a reservoir being coated with an inert silicon-based coating for transporting a volume of an aqueous ionic mercury solution to a liquid mass flow controller and vaporizer for generating a mercury ionic gas standard.

The United States Environmental Protection Agency (EPA) identifies sources of mercury (Hg) emissions in the U.S. to be utility boilers, waste incinerators that burn mercury-containing wastes (municipal and medical), coal-fired industrial boilers and cement kilns that burn coal-based fuels. A particularly significant source of mercury emissions is coal-fired power plants.

To quantify the emissions from a particular source, a continuous emissions monitoring system (CEMS) is employed for mercury. There are three forms of mercury in exhaust flue gas streams of a coal-fired power plant that may be monitored by a CEMS. These forms are gaseous elemental mercury, gaseous oxidized mercury and particulate bound mercury that is either elemental or oxidized, at stack gas temperatures in excess of 200° F.

Current continuous emissions monitoring systems for mercury using a mercuric chloride liquid standard solution use a peristaltic pump for transporting the mercuric chloride to a liquid mass flow controller and vaporizer. These systems are difficult to use as there can be numerous problems such as tube failure with the peristaltic pumps. For example, in many instances the tube of the peristaltic pump can become clogged or blocked, leading to inconsistencies in delivering the mercuric chloride liquid standard solution to the liquid mass flow controller. This can lead to inaccuracies in the measurements as the efficient mixing of mercuric chloride with the carrier gas (e.g., air or nitrogen) can be questionable.

Additionally, the tubing of the peristaltic pump can tear, requiring expensive maintenance. Furthermore, a torn tube can cause wear and tear on the pump motor itself requiring additional maintenance.

As such, there is a need in the art for the development of a reliable and accurate technology capable of measuring the levels of mercury emitted in an exhaust flue gas stream. More specifically, there is a need for an alternative means of transporting the mercuric chloride liquid standard solution to the liquid mass flow controller and vaporizer without utilizing the peristaltic pump. It would be advantageous if the means could lead to improved accuracy in measuring mercury levels and did not require extensive maintenance such as those for systems using the peristaltic pump.

BRIEF DESCRIPTION OF THE INVENTION

The present disclosure relates to a mercury ionic gas standard generator that incorporates a reservoir being coated with an inert silicon-based coating for transporting a volume of an aqueous ionic mercury solution to a liquid mass flow controller and vaporizer. Once the aqueous ionic mercury solution has been heated and atomized with a pressurized carrier gas (e.g., air or nitrogen), the atomized standard can be forced into a heated line that is in fluid connection with a flue stack for analysis. The inert silicon-based coated reservoir of the mercury ionic gas standard generator of the present disclosure can replace the need for the peristaltic pump conventionally used in these generator-type devices and proven to cause numerous operating and maintenance problems.

As such, the present disclosure is directed to an improved mercury ionic gas standard generator for use in a continuous emissions monitoring system. The mercury ionic gas standard generator comprises an inert silicon-based coated reservoir; a liquid mass flow controller; and a vaporizer. In addition to the inert silicon-based coating, the reservoir also comprises an aqueous ionic mercury solution. The liquid mass flow controller comprises an aqueous stabilizer.

The present disclosure is further directed to a mercury ionic gas standard generator comprising: a reservoir comprising an inert silicon-based coating applied thereto, the reservoir further comprising an aqueous mercury chloride solution and a first pressurized gas therein; a liquid mass flow controller comprising an aqueous stabilizer and a second pressurized gas; and a vaporizer.

The present disclosure is additionally directed to the method of using the mercury ionic gas standard generator for generating a mercury ionic gas standard for use with a continuous emissions monitoring system. Specifically, in one embodiment, the present disclosure is directed to a method of generating a mercury ionic gas standard, the method comprising: introducing a first pressurized gas into a reservoir, the reservoir comprising an inert silicon-based coated and an aqueous ionic mercury solution, to force the aqueous ionic mercury solution into a liquid mass flow controller; introducing a second pressurized gas into the liquid mass flow controller comprising the aqueous ionic mercury solution to force the second pressurized gas and the aqueous ionic mercury solution into a vaporizer; and heating and atomizing the second pressurized gas and the aqueous ionic mercury solution in the vaporizer to form heated atomized liquid droplets.

Other objects and features will be in part apparent and in part pointed out hereinafter.

DETAILED DESCRIPTION OF THE INVENTION

Figure 1:
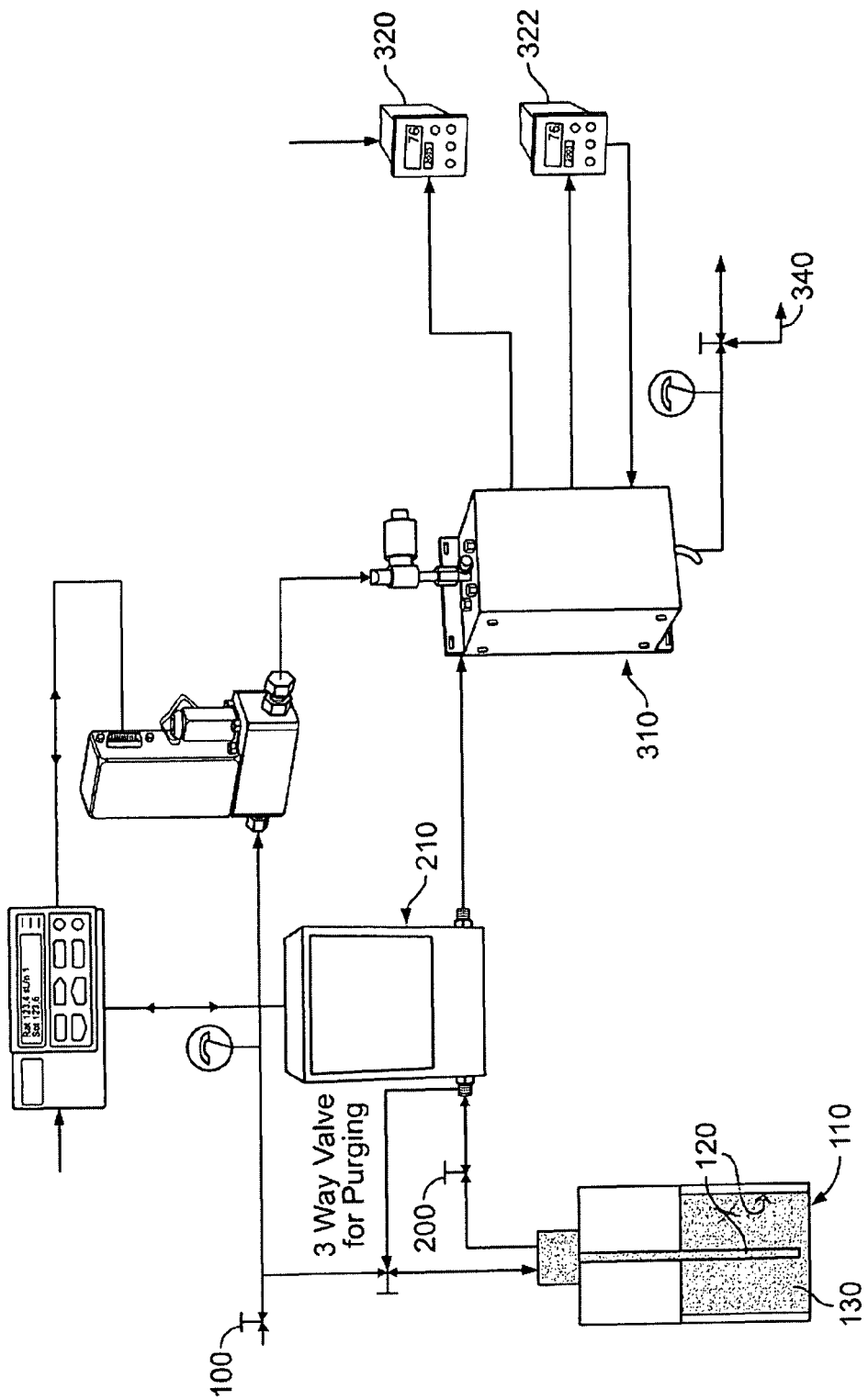
FIG. 1 is a schematic of a mercury ionic gas standard generator of the present disclosure for generating a mercury ionic gas standard.

The present disclosure is generally related to the use of an improved mercury ionic gas standard generator for use with the continuous emissions monitoring of mercury in exhaust flue gas streams. More specifically, the present disclosure relates to the use of a reservoir being coated with an inert silicon-based coating for transporting a volume of an aqueous ionic mercury solution to a liquid mass flow controller and vaporizer. Once the aqueous ionic mercury solution has been heated and atomized with a pressurized carrier gas (e.g., air or nitrogen), the atomized standard can be forced into a heated line that is in fluid connection with a flue stack for analysis. Typically, the atomized aqueous ionic mercury solution is forced into the heated line using pressurized gas (e.g., air or nitrogen).

A continuous emissions monitoring system (CEMS) for mercury normally consists of a tubular probe assembly connecting a flue stack for acquiring a gaseous exhaust sample. The CEMS also includes instrumentation, i.e., the mercury ionic gas standard generator, located some distance away from the probe assembly to generate a mercury ionic gas standard to analyze the acquired sample for the presence of mercury. The relatively small concentration of mercury present in the exhaust gas stream is continuously measured and recorded. Over time, the total amount of mercury emitted is established. As such, accuracy and precision of the continuous emissions monitoring system, and particularly, the mercury ionic gas standard generator, is important.

The mercury ionic gas standard generator of the present disclosure includes: an inert silicon-based coated reservoir; a liquid mass flow controller; and a vaporizer. Typically, the reservoir is a refillable pressure vessel made of stainless steel. Typically, the refillable pressure vessel is from about 500 to about 1000 milliliters in size.

As noted above, the inner surface of the reservoir is coated using any method known in the art (e.g., spraying, painting, or the like) with an inert silicon-based coating. The coating prevents the chemical interaction of the aqueous ionic mercury solution, as described more fully below, from interacting with any of the internal sides of the reservoir. Particularly preferred inert silicon-based coatings are Silcosteel-CR® and Siltek®, both commercially available inert coatings from Restek Corporation, Bellefonte, Pa. The Silcosteel-CR® has additionally shown particularly heavy corrosion resistance.

The amount of coating on the inner surface of the reservoir can be any suitable amount known in the art of coatings and will typically vary depending upon the size of the reservoir and the amount of aqueous ionic mercury solution to be introduced into the reservoir. Typically, the inner surface of the reservoir will be coated with the coating at a thickness of from about 1 millimeter to about 3 millimeters, more suitably from about 1 millimeter to about 2 millimeters.

The inert silicon-based coated reservoir of the mercury ionic gas standard generator of the present disclosure can replace the need for the peristaltic pump conventionally used in these generator devices. As noted above, conventional devices have had numerous operating and maintenance problems due to the clogging and tearing of the various moving parts of the peristaltic pump. These problems are now eliminated by using the inert silicon-based coated reservoir in combination with a pressurized gas for forcing an aqueous ionic mercury solution into a liquid mass flow carrier, as described more fully below. More particularly, the pressurized gas alone can force the aqueous ionic mercury solution through the mercury ionic gas standard generator, thereby eliminating the need for moving parts and parts that wear out, which can affect the reliability and accuracy of the device.

The aqueous ionic mercury solution can be any aqueous ionic mercury solution known to one skilled in the art. Typically, the aqueous ionic mercury solution is used in a concentration of from about $10^{-6}$ moles per liter to about $10^{-10}$ moles per liter. More specifically, the aqueous ionic mercury solution can be used in a concentration of from about $10^{-6}$ moles per liter to about $10^{-9}$ moles per liter. One particularly preferred aqueous ionic mercury solution is aqueous mercury chloride.

The mercury ionic gas standard generator also includes a liquid mass flow controller. The liquid mass flow controller moves the aqueous ionic mercury solution received from the reservoir to the vaporizer. Additionally, the liquid mass flow controller forces a pressurized gas into the vaporizer to be mixed with the aqueous mercury solution. One particularly preferred liquid mass flow controller is the Quantim® Coriolis Mass Flow Controller with Hastelloy Coriolis Tube, commercially available from Brooks Instrument, a division of Emerson Process Management, Hatfield, Pa. The Quantim Coriolis Mass Flow Controller typically operates at a maximum temperature of approximately 65° C. The electrical flow rate input is from about 4 mA to about 20 mA and the electrical flow rate output is from about 4 mA to about 20 mA.

Generally, the liquid mass flow controller comprises an aqueous stabilizer for the aqueous ionic mercury solution. Any stabilizer for the aqueous ionic mercury solution known in the art is suitable for use as the aqueous stabilizer. One particularly preferred aqueous stabilizer is hydrochloric acid. More particularly, a 1 molar (M) solution of hydrochloric acid is particularly suitable for use in the liquid mass flow controller used in the mercury ionic gas standard generator of the present disclosure. Another suitable stabilizer is nitric acid.

Along with the inert silicon-based coated reservoir and the liquid mass flow controller, the mercury ionic gas standard generator of the present disclosure further includes a vaporizer for heating and atomizing the aqueous ionic mercury solution with a carrier gas, as described below. Any vaporizer known in the art of continuous emissions monitoring (CEM) can be used in the mercury ionic gas standard generator of the present disclosure. One particularly preferred vaporizer is a MSP TurboVaporizer®, commercially available from Brooks Instrument, a division of Emerson Process Management, Hatfield, Pa. The MSP TurboVaporizer® contains a 200-watt, 120 VAC heater and is capable of heating and atomizing more than 5 grams of an aqueous ionic mercury solution per minute. The MSP TurboVaporizer thus accommodates a much higher flow rate than needed of the mercury ionic gas standard generator of the present disclosure. As such, it should be understood in the art that a smaller, less expensive vaporizer could also be used without departing from the scope of the present disclosure.

Now referring to FIG. 1, the mercury ionic gas standard generator as described above is used for generating a mercury ionic gas standard for a continuous emissions monitoring system. Specifically, to begin, a first pressurized gas 100 is introduced into a reservoir 110. The reservoir 110 includes an inert silicon-based coating 120 along its inner walls and an aqueous ionic mercury solution 130. Typically, the first pressurized gas 100 is pressurized and pushed into the reservoir 110 using an air compressor or pressurized gas cylinder (not shown). The first pressurized gas 100 is under a pressure of from about 0.5 psi to about 4.0 psi. More suitably, the first pressurized gas is under a pressure of from about 1.0 psi to about 2.0 psi.

Suitable gas for use as the first pressurized gas can include air, argon, and nitrogen. In a particularly preferred embodiment, the gas is air. Air is typically preferred as clean air is significantly less expensive to use as compared to the other gasses.

Once introduced into the reservoir 110, the first pressurized gas 100 forces the aqueous ionic mercury solution 130 out of the reservoir 110 into a liquid mass flow controller 210. Typically, the aqueous ionic mercury solution 130 is forced into the liquid mass controller 210 at a flow rate of from about 0.1 gram per minute (g/min) to about 4.0 g/min. More suitably, the aqueous ionic mercury solution 130 is forced into the liquid mass controller 210 at a flow rate of about 1.5 g/min.

Along with the aqueous ionic mercury solution 130, a second pressurized gas (also referred to herein as a pressurized carrier gas) 200 is introduced into the liquid mass flow controller 210. As with the first pressurized gas 100 described above, the second pressurized gas 200 is pressurized and pushed into the liquid mass flow controller 210 using an air compressor or pressurized gas cylinder (not shown). The second pressurized gas 200 is typically under a pressure of from about 20 psi to about 90 psi. More suitably, the second pressurized gas 200 is under a pressure of about 45 psi.

Suitable gas for use as the second pressurized gas can include, for example, air and nitrogen. In a particularly preferred embodiment, the gas is air. Air is typically preferred as clean air is significantly less expensive to use as compared to other gasses.

As noted above, the liquid mass flow controller 210 typically contains an aqueous stabilizer (not shown) such as hydrochloric acid or nitric acid to prevent the aqueous ionic mercury solution 130 from interacting with the sides of the liquid mass flow controller 210.

From the liquid mass flow controller 210, the second pressurized gas (i.e., pressurized carrier gas) 200 and aqueous ionic mercury solution 130 are forced to the vaporizer 310 wherein the second pressurized gas 200 and aqueous ionic mercury solution 130 are heated and atomized. Typically, the vaporizer is heated for about 10 minutes to about 45 minutes prior to the introduction of the pressurized gas 200 and aqueous ionic mercury solution 130.

Suitably, the second pressurized gas 200 is forced into the vaporizer 310 at a flow rate of from about 0.1 liters per minute (L/min) to about 20 L/min. The aqueous ionic mercury solution 130 is suitably forced into the vaporizer 310 at a flow rate of from about 0.1 g/min to about 4.0 g/min.

The second pressurized gas 200 and aqueous ionic mercury solution 130 are heated to a temperature of at least 180° C. in the vaporizer 310. In one particularly preferred embodiment, the second pressurized gas 200 and aqueous ionic mercury solution 130 are heated to a temperature of from 180° C. to about 200° C. The temperature of the vaporizer 310 can be controlled using at least one temperature limit controller. In one embodiment, as shown in FIG. 1, there are two temperature limit controllers 320 and 322. Specifically, a first temperature limit controller 320 monitors the temperature within the vaporizer 310 and a second temperature limit controller 322 controls the heater (not shown) to maintain the temperature of the vaporizer 310.

Typically, the second pressurized gas and the aqueous ionic mercury solution are heated continuously in the vaporizer for a residence time period of from about 0.1 seconds to about 3 seconds.

Under these conditions, the vaporizer 310 heats and atomizes the second pressurized gas 200 and the aqueous ionic mercury solution 130 nearly instantaneously to form heated atomized liquid droplets. The liquid droplets are suitably aerosol-type droplets (not shown) having a size of from about 2 microns to about 5 microns.

Once the liquid droplets are formed, the droplets are forced out of the vaporizer into a heated line (not shown). Typically, the liquid droplets are forced out of the vaporizer at a rate of from about 20 psig to about 100 psig, more suitably, at a rate of from about 20 psig to about 30 psig. In one embodiment, as shown in FIG. 1, the vaporizer 310 consumes energy in such an amount as to require ventilation. As such, a vent 340 is coupled to the vaporizer 310. It should be understood by one skilled in the art, that while shown with a vent 340, the vaporizer 310 may not require ventilation without departing from the scope of the present disclosure.

The heated line is in fluid connection with a flue stack (not shown) for analysis. Specifically, the heated line is typically part of a tubular probe assembly located in fluid connection with a flue stack for acquiring a gaseous exhaust sample. The heated line typically runs from about 5 feet to about 1000 feet, and more suitably, 50 feet to about 600 feet, to connect the mercury ionic gas standard generator to the flue stack for analysis.

When introducing elements of the present disclosure or preferred embodiments thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions and methods without departing from the scope of the disclosure, it is intended that all matter contained in the above description and shown in the accompanying drawings shall be interpreted as illustrative and not in a limiting sense.

What is claimed is:

1. A method of generating a mercury ionic gas standard for use with a continuous emissions monitoring system, said method comprising:

pushing a first pressurized gas from a first gas source, using a first air compressor, into a reservoir that includes an inert silicon-based coating applied along an inner surface of the reservoir and an aqueous ionic mercury solution to force the aqueous ionic mercury solution into a liquid mass flow controller;

introducing a second pressurized gas from a second gas source into the liquid mass flow controller that includes the aqueous ionic mercury solution to force the second pressurized gas and the aqueous ionic mercury solution into a vaporizer; and heating and atomizing the second pressurized gas and the aqueous ionic mercury solution in the vaporizer to form heated atomized liquid droplets.

2. The method as set forth in claim 1 wherein the first pressurized gas is under a pressure of from about 0.5 psi to about 4.0 psi.

3. The method as set forth in claim 1 wherein the aqueous ionic mercury solution is an aqueous mercury chloride solution.

4. The method as set forth in claim 1 wherein the aqueous ionic mercury solution is forced into the liquid mass flow controller at a flow rate of from about 0.1 g/min to about 4 g/min.

5. The method as set forth in claim 1 wherein the liquid mass flow controller comprises a stabilizer.

6. The method as set forth in claim 1 wherein the second pressurized gas is under a pressure of from about 20 psi to about 90 psi.

7. The method as set forth in claim 1 wherein the second pressurized gas is forced into the vaporizer at a flow rate of from about 0.1 L/min to about 20 L/min.

8. The method as set forth in claim 1 wherein the aqueous ionic mercury solution is forced into the vaporizer at a flow rate of from about 0.1 g/min to about 4 g/min.

9. The method as set forth in claim 1 wherein the first pressurized gas and the second pressurized gas are independently selected from the group consisting of air and nitrogen.

10. The method as set forth in claim 1 wherein the second pressurized gas and the aqueous ionic mercury solution are heated in the vaporizer at a temperature of at least 180° C.

11. The method as set forth in claim 1 wherein the second pressurized gas and the aqueous ionic mercury are atomized in the vaporizer to form liquid droplets having a size of from about 2 to about 5 microns.

* * * * *